(12) United States Patent
Hembre

(10) Patent No.: US 6,448,431 B1
(45) Date of Patent: Sep. 10, 2002

(54) PRODUCTION OF ARYL CARBOXYLATE ESTERS

(75) Inventor: Robert Thomas Hembre, Johnson City, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/528,592

(22) Filed: Mar. 20, 2000

Related U.S. Application Data

(60) Provisional application No. 60/153,240, filed on Sep. 13, 1999.

(51) Int. Cl.$^7$ .............................................. C07C 69/00
(52) U.S. Cl. ...................... 560/130; 562/887; 554/151; 554/161; 554/229; 558/56
(58) Field of Search .................. 560/130; 562/887; 554/151, 161, 229; 558/56

(56) References Cited

U.S. PATENT DOCUMENTS

| | | |
|---|---|---|
| 2,082,790 A | 6/1937 | Cherry |
| 3,772,389 A | 11/1973 | Lowrance, Jr. |
| 3,923,857 A | 12/1975 | Boller et al. |
| 4,478,754 A | 10/1984 | Kong-Chan |
| 4,537,724 A | 8/1985 | McKinnie et al. |
| 4,587,054 A | 5/1986 | Hardy et al. |
| 4,588,532 A | 5/1986 | Moyne et al. |
| 4,735,740 A | 4/1988 | Zielske |
| 4,883,612 A | 11/1989 | Moyne et al. |
| 5,069,828 A | 12/1991 | Dumas et al. |
| 5,332,858 A | 7/1994 | De Jong et al. |
| 5,523,434 A | 6/1996 | Burns et al. |
| 5,534,642 A | 7/1996 | Heinzman et al. |
| 5,650,527 A | 7/1997 | Lutz et al. |

FOREIGN PATENT DOCUMENTS

| | | |
|---|---|---|
| DE | 3824901 | 2/1990 |
| EP | 105672 | 4/1984 |

OTHER PUBLICATIONS

Allan H. Gilbert, Detergent Age, Jun., 1967, pp. 18–20.
Allan H. Gilbert, Detergent Age, Aug., 1967, pp. 26–28.
William W. Lowrance, Jr., Tetrahedron Letters, 1971, No. 37, pp. 3453–3454.
E. J. Bourne et al., J. Chem. Soc., 1949, pp. 2976–2979.
Thomas C. Bruice et al., Journal of American Chemical Society, 1968, 90, pp. 1333–1348.
E. J. Bourne et al., J. Chem. Soc., 1954, pp. 2006–2012.

Primary Examiner—Paul J. Killos
(74) Attorney, Agent, or Firm—Michael J. Blake

(57) ABSTRACT

Disclosed is a process for the preparation of aryl carboxylate esters by the reaction of a phenol reactant with an esterification agent selected from carboxylic acid anhydrides and carboxylic acid halides in the presence of trifluoroacetic acid (TFA).

16 Claims, No Drawings

PRODUCTION OF ARYL CARBOXYLATE ESTERS

CROSS REFERENCE TO RELATED APPLICATIONS

This application claims the benefit of U.S. Provisional Application No. 60/153,240, filed Sep. 13, 1999.

FIELD OF THE INVENTION

This invention pertains to a process for the preparation of aryl carboxylate esters. More specifically, this invention pertains to a process for preparing aryl carboxylate esters by the reaction of a phenol reactant with a carboxylic esterification agent selected from carboxylic acid anhydrides and carboxylic acid halides in the presence of trifluoroacetic acid (TFA).

BACKGROUND OF THE INVENTION

Aryl carboxylate esters such as phenolsulfonate esters are useful bleach activators (Allan H. Gilbert, *Detergent Age*, 1967, June, pages 18–20 and August, pages 30–33). Aryl carboxylate esters also are of commercial interest useful as components of liquid crystals and polyarylate liquid crystal polymers. A number of methods for synthesizing aryl carboxylate esters are described in the literature. These known procedures, in general, require relatively harsh conditions and proceed slowly to completion. For example, the reaction of a carboxylic acid with a phenol driven by the removal of water to produce aryl carboxylates via boric acid catalysis is described by William W. Lowrance in *Tetrahedron Letters*, 1971, 37, 3453 and in U.S. Pat. No. 3,772,389. A similar boric acid catalyzed phenolsulfonate ester synthesis is described in U.S. Pat. No. 4,478,754 and requires many hours at temperatures greater than 180° C. Related procedures employing the reaction of a carboxylic acid with a aryl ester (transesterification by alcoholysis or acidolysis) have been published. U.S. Pat. Nos. 4,537,724 and 5,534,642 and European Patent Publication 105,672 disclose such processes but these also require harsh conditions, i.e. many hours at temperatures from 160–300° C.

More active carboxylic acid derivatives such as acid chlorides and anhydrides react with an alkali metal salt of phenolsulfonate, e.g., sodium 4-phenolsulfonate (SPS) under milder conditions. These reactions are carried out either in a solvent or the carboxylic acid related to the desired ester product at temperatures of 80 to 200° C. The use of carboxylic acid anhydrides as the esterification agent is the preferred route for commercial scale synthesis.

U.S. Pat. No. 4,587,054 discloses the reaction of a $C_6$–$C_{18}$ carboxylic acid anhydride and substituted phenol at temperatures between 80–120° C. using strong acid catalysis or at temperatures between 180–220° C. using base catalysis. Similarly, U.S. Pat. Nos. 4,588,532 and 4,883,612 describe the reaction of a $C_7$–$C_{12}$ carboxylic acid anhydride in a polar aprotic solvent with SPS in the presence of a catalytic amount of sulfonic acid at temperatures "in excess of about 100° C." An example illustrates the operation of the process at 115 to 120° C. for a period of six hours. A disadvantage of strong acid-catalyzed processes is the coincident catalysis of desulfonation of the phenolsulonate reactant leading to yield losses and darker colored products. U.S. Pat. Nos. 4,588,532 and 4,883,612 also disclose a base-catalyzed process also using a polar aprotic solvent "in excess of 80° C." An example describes a base-catalyzed experiment carried out at 90° C. for three hours. U.S. Pat. No. 5,534,642 discloses the reaction of an amido-substituted carboxylic acid anhydride with a phenolsulfonate salt at 180° C. for 3 hours.

The synthesis of aryl alkanoate esters using an "impeller esterification" technique is known. For example, U.S. Pat. No. 2,082,790 discloses the simultaneous addition of acetic anhydride ($Ac_2O$) to a mixture of an alkanoic acid and a phenol to produce the aryl alkanoate ester. The "$Ac_2O$ impeller" method for the synthesis of phenolsulfonate esters is disclosed in U.S. Pat. Nos. 4,735,740 and 5,650,527, German Patent Publication DE 3,824,901 A1, and European Patent Publication EP 105,672. In each of the processes disclosed in these patent documents, $Ac_2O$ is added to a carboxylic acid of low volatility in the presence of SPS, heated for an extended period of time at relatively high temperatures, e.g., 2–5 hours at temperatures greater than 120° C., and acetic acid is removed at reduced pressure to drive the conversion of SPS to its carboxylic acid ester. This method thus also requires prolonged treatment at relatively high temperature to achieve acceptable reaction yields.

An improved impeller method for the synthesis of aryl alkanoate was introduced by E. J. Bourne and coworkers in Journal of the Chemical Society 1949, 2976–79. Bourne et al. disclose the use of trifluoroacetic anhydride (TFAA) in the synthesis of aryl alkanoate esters using milder conditions. The use of the TFAA impeller esterification method for the synthesis of a phenolsulfonate ester was first disclosed by Thomas C. Bruice et al. in the J. Am. Chem. Soc., 1968, 90, 1333–48. Bruice at al. disclose treatment of decanoic acid and SPS with TFM at somewhat milder conditions (80° C., 5 hours) than those reported for the $Ac_2O$ impeller method but do not report reaction yields. TFAA, however, presently is an expensive chemical and economic considerations discourage its use in large-scale synthesis.

The use of carboxylic acid chlorides for the synthesis of aryl carboxylate liquid crystals is disclosed in U.S. Pat. No. 3,923,857 and in the synthesis of polyarylate polymers in U.S. Pat. No. 5,332,858. These patents disclose the use of very mild conditions (25–80° C.) but require the use of reagents such as pyridine or catalysts such as tin tetrachloride which complicate product purification. U.S. Pat. No. 5,069,828 discloses procedures for the synthesis of phenolsulfonate esters using acid chlorides which require prolonged reaction times at temperatures from 80 to 200° C. Such conditions are known in the art to lead to formation of undesirable color bodies in the product. The use of Schotten-Baumann conditions (pH=9–10, 5–20° C.) to produce phenolsulfonate esters is described in U.S. Pat. No. 5,523,434 but the reaction yields are compromised under these conditions.

A need thus exists for synthetic methods to produce aryl carboxylate esters under mild conditions, i.e. temperatures less than 80° C., which are appropriate for large-scale synthesis. In particular, high-yield methods are needed for the synthesis of phenolsulfonate esters which minimize the production of color bodies and provide for efficient methods of product purification.

BRIEF SUMMARY OF THE INVENTION

I have discovered that the reaction of carboxylic acid anhydrides and carboxylic acid halides with phenols proceeds at improved rates under milder conditions than previously reported when the reaction is carried out in the presence of TFA. The process of the present invention therefore comprises the preparation of an aryl carboxylate ester by reacting a phenol with an esterification agent selected from carboxylic acid anhydrides containing a total of up to about 40 carbon atoms and carboxylic acid halides containing a total of up to about 20 carbon atoms in the presence of TFA, wherein the amount of TFA present initially and during the process gives a TFA:phenol reactant mole ratio of at least about 0.5:1. The process of the present invention utilizes a phenol reactant, an esterification agent and TFA and normally is carried out in the absence of trifluoroacetic anhydride and other perfluorocarboxylic acid anhydrides. The process also is operated under substantially anhydrous conditions to avoid decomposition of the carboxylic anhydride and halide esterification agents.

A second embodiment of the present invention is directed to the use of mixed anhydrides as the esterification agent in the preparation of aryl carboxylate esters by the esterification of a phenol. Such mixed anhydrides are produced by the reaction of TFA with the carboxylic acid anhydrides containing a total of up to about 40 carbon atoms and carboxylic acid halides containing a total of up to about 20 carbon atoms utilized in the embodiment described above. The second embodiment therefore comprises the preparation of an aryl carboxylate ester by reacting a phenol with a mixed anhydride having the formula:

$$R\text{—}C(O)\text{—}O\text{—}C(O)\text{—}CF_3 \qquad (I)$$

in the presence of TFA, wherein R is an aliphatic, cycloaliphatic or aromatic group containing up to about 19 carbon atoms; and the amount of TFA present initially and during the process gives a TFA:phenol reactant mole ratio of at least about 0.5:1. Mixed anhydride (I) may be formed in situ by bringing TFA and a carboxylic acid anhydride or halide into contact or it may be formed separately and used subsequently in the process of producing an aryl carboxylate ester.

The solvent properties of TFA make it the preferred solvent for the preparation of phenolsulfonate esters, especially sodium and potassium phenolsulfonate esters. Highly concentrated solutions, e.g., 20–50 weight percent, of phenolsulfonate esters can be produced. Such high solubility combined with efficient solvent separation due to the low boiling point of TFA (72° C.) make it uniquely suited to the manufacture of phenolsulfonate esters.

Because the esterifications in TFA in accordance with the present invention occur under very mild conditions, the common problem of color formation is not encountered. Likewise, these methods can be applied to the synthesis of a wide variety of phenol esters, including phenol esters wherein the carboxylate residue is substituted, e.g., an alkanoylamido-substituted carboxylate residue. The process of the present invention may be used with difunctional compounds such as dicarboxylic acid anhydrides, e.g., succinic and phthalic anhydride, and dicarboxylic acid dihalides, e.g., adipic acid dichloride, and/or aromatic diols, e.g., hydroquinone and resorcinol, that are of interest in the preparation of polymeric materials. In most cases, the isolation and purification of products is reduced to simply removing the TFA by evaporation and then washing the product with a second solvent such as methanol or acetone. In the manufacture of phenolsulfonate esters TFA may be removed with a solvent substitution procedure using a higher boiling liquid, e.g., propionic acid, having low solvent properties for phenolsulfonate esters to produce a filterable, purified solid product. As mentioned, certain of the carboxylate esters which may be prepared by the present process are useful as bleach activators while others, especially arylene dicarboxylates and diaryl dicarboxylates, are useful in the preparation of polymers. The carboxylate esters also are useful as esterification agents for producing a variety of esters.

DETAILED DESCRIPTION

The process of provided by the present invention is a process for the preparation of an aryl carboxylate ester which comprises contacting or reacting a phenol with an esterification agent selected from carboxylic acid anhydrides and carboxylic acid halides in the presence of TFA, wherein the amount of TFA present initially and during the process gives a TFA:phenol reactant mole ratio of at least about 0.5:1. The esterification agent also may be a mixed anhydride having the formula:

$$R\text{—}C(O)\text{—}O\text{—}C(O)\text{—}CF_3 \qquad (I)$$

The phenol reactant may be unsubstituted phenol or naphthol or a hydroxybenzene or hydroxynapthalene compound which may be substituted with a variety of substituents, usually not more than two, such as alkyl of up to about 12 carbon atoms, alkoxy containing up to about 12 carbon atoms, halogen such as chloro and bromo, sulfo, an alkali metal salt of sulfo such as sodium and potassium sulfo salts, alkanoylamido containing up to about 12 carbon atoms, nitro, formyl, cyano and the like. The phenol reactant also may be substituted with a second hydroxy group, i.e., 1,2-, 1,3- and 1,4-benzenediols which result in the formation of arylene bis(alkanoate) esters. Additional aromatic diols which may be used include 1,4-naphthalenediol, 4,4'-sulfonyldiphenol and 4,4'-biphenol. The phenol reactant preferably is unsubstituted phenol or an alkali phenolsulfonate, especially sodium phenolsulfonate. The unsubstituted phenyl ester produced in accordance with the present invention may be sulfonated to prepare the alkali metal phenolsulfonate ester which are useful as bleach activators.

The esterification agent may be an unsubstituted or substituted aliphatic carboxylic acid anhydride containing up to about 40 carbon atoms or an unsubstituted or substituted aliphatic, cycloaliphatic or aromatic carboxylic acid halide containing a total of up to about 20 carbon atoms. The unsubstituted aliphatic carboxylic acid anhydrides, preferably unsubstituted alkanoic acid anhydrides, typically contain 8 to 36, preferably about 12 to 32, carbon atoms. The unsubstituted aliphatic carboxylic acid halides, e.g., chlorides and bromides, preferably unsubstituted alkanoic acid halides, typically contain 4 to 18, preferably about 6 to 16, carbon atoms. The alkanoic acid halides and the alkanoic acid residues of the carboxylic acid anhydrides, e.g., a saturated, aliphatic carboxylic acid anhydride or halide, may be substituted with one or more, typically one, substituent selected from alkoxy containing up to about 12 carbon atoms, halogen such as chloro and bromo, alkanoylamido containing up to about 12 carbon atoms, aryl such as phenyl and phenyl substituted with alkyl, alkoxy and/or halogen. The alkanoic acid halides may be substituted with a second carboxyl group, e.g., adipic acid dichloride, azelaic acid dichloride and the like, which results in the formation of diaryl dialkanoate esters. The esterification agent preferably is an alkanoic acid anhydride wherein each of the two alkanoic acid residues of the anhydride contains about 6 to 16 carbon atoms and is either unsubstituted or is substituted with an alkanoylamido group containing up to about 12 carbon atoms. The esterification agent also may be selected from cycloaliphatic and aromatic, carbocyclic, carboxylic acid anhydrides and halides wherein each carboxylic acyl residue contains from about 6 to 20 carbon atoms. Examples of such cycloaliphatic and aromatic, carbocyclic, carboxylic acid anhydrides and halides include cyclohexanecarboxylic acid chloride and bromide, benzoyl chloride, and the naphthalenecarboxylic acid halides which may be unsubstituted or substituted with a wide variety, usually not more than two, of substituents such as alkyl of up to about 12 carbon atoms, alkoxy containing up to about 12 carbon atoms, halogen such as chloro and bromo, sulfo, an alkali metal salt of sulfo such as sodium and potassium sulfo salts, alkanoylamido containing up to about 12 carbon atoms, nitro, formyl, cyano and the like. The cycloaliphatic and aromatic, carbocyclic, carboxylic acid halides also may be dicarboxylic acid dihalides such as 1,2-, 1,3- and 1,4-cyclohexanedicarboxylic acid dichloride, 1,2-, 1,3- and 1,4-benzenedicarboxylic acid dichloride, 1,2-benzenedicarboxylic acid anhydride and the many naphthalenedicarboxylic acid halide isomers. The carboxylic acid anhydride and phenol may be used in anhydride:phenol mole ratios in the range of about 0.5:1 to 3:1, preferably about 0.8:1 to 1.2:1.

The anhydride and acid chloride esterification agents are commercially available and/or can be prepared from the corresponding carboxylic acid by known procedures, e.g., by contacting the corresponding carboxylic acid with (i) acetic anhydride to prepare the anhydride esterification agents or (ii) phosphorus trichloride or tribromide to prepare the acid halide esterification agents.

The R-group of the mixed anhydride having the formula:

R—C(O)—O—C(O)—CF$_3$ (I)

Is the residue of the carboxylic acid residues described herein. Thus, R may represent an aliphatic, cycloaliphatic or aromatic group containing up to about 19 carbon atoms which may be unsubstituted or substituted as described above. The R residue preferably contains about 5 to 15 carbon atoms and is either unsubstituted or is substituted with an alkanoylamido group containing up to about 12 carbon atoms.

Mixed anhydride (I) may be prepared by (i) the addition of trifluoroacetate salts to carboxylic acid halides (Ferris et al., *J. Am. Chem. Soc.* 1952, 75, 232), (ii) the reaction of trifluoroacetic anhydride (TFAA) with a carboxylic anhydride (Bourne, et al., J. Chem. Soc. 1954, 2006) or (iii) the reaction of TFM with a carboxylic acid (Emmons, et al., *J. Am. Chem. Soc.* 1953, 75, 6047) and purified by distillation. Examples of these procedures are given herein. The generation of TFA mixed anhydrides via equilibria between carboxylic anhydrides and TFA has been studied by Bonner, et al., *Tetrahedron* 1965, 21, 463. Although such equilibria may only generate low concentrations of such mixed anhydrides the high reactivity of these species provide for their practical application in the synthesis of aryl carboxylate esters. Similar, equilibria may exist between carboxylic acid halides and TFA. Likewise, related equilibria may exist between other carboxylic acid derivatives and TFA mixed anhydrides when said carboxylic acid derivatives are dissolved in a solvent containing TFA.

The amount of TFA solvent present initially and during the operation of the process of the present invention typically gives a TFA:phenol reactant mole ratio of at least 0.5:1 and preferably a TFA:phenol mole ratio in the range of about 2:1 to 20:1. Such mole ratios typically provide preferred amounts of TFA greater than 15 weight percent based on the weight of the phenol reactant, esterification agent and TFA present. The amount of TFA present preferably is in the range of about 30 to 80 weight percent based on the weight of the phenol, esterification agent and TFA present. Other inert solvents may be used in conjunction with TFA.

Examples of such solvents include halogenated hydrocarbons such as dichloromethane and dichloro-benzene; ethers such as diethylether and diglyme; aromatic hydrocarbons such as toluene; and polar aprotic solvents such as dimethylformamide, acetonitrile and sulfolane.

The solvent properties of TFA are unique and highly advantageous in the synthesis of phenolsulfonate esters. Exemplary data showing the solubility of 4-(nonanoyloxy) benzenesulfonate (NOBS) in a series of solvents is displayed in Table 1 wherein solubilities were measured at 23° C. and expressed as grams of NOBS soluble in 100 grams of solution. It is notable that the only solvent in which NOBS is more soluble than water is TFA. I have found no better solvent for NOBS than TFA. This is surprising. First, examination of solvents 2–7 in Table 1 shows a reasonable correlation of NOBS solubility with solvent polarity. TFA is a non-polar solvent with a dielectric constant similar to that of acetic acid yet it dissolves more than ten times the amount of NOBS which is soluble in acetic acid at ambient temperature. It is likely that hydrogen bonding in TFA facilitates the solvation of sulfonate anions but it is notable, in contrast, that such effects are much weaker in acetic acid. Furthermore, while it is known in the art that dimethyl sulfoxide (DMSO) and dimethylformamide (DMF) are relatively good solvents for benzenesulfonate esters they are much weaker solvents than TFA and because TFA has a much lower boiling point than these dipolar aprotic solvents it is the only good solvent for benzenesulfonate esters which can be readily stripped from product solutions and then purified and recycled with relative ease.

TABLE 1

Solubility of NOBS in Selected Solvents

|   | wt % NOBS | Dielectric Constant | normal b.p. |
|---|---|---|---|
| 1. TFA | 23.4 | 8.3 | 71.8 |
| 2. water | 22.8 | 78.3 | 100.0 |
| 3. DMSO | 15.9 | 46.4 | 189.0 |
| 4. DMF | 10.1 | 36.7 | 153.0 |
| 5. NMP | 8.4 | 32.2 | 202.0 |
| 6. acetic acid | 1.7 | 6.2 | 117.9 |
| 7. nonanoic acid | 0.03 | 1.7 | 254.0 |
| 8. acetone | 0.02 | 20.6 | 56.1 |
| 9. acetonitrile | 0.01 | 35.9 | 81.6 |

In Table 1, the dielectric constants and boiling points for solvents 2–6 and 8–9 were taken from Christian Reichardt *Solvent and Solvent Effects in Organic Chemistry;* VCH: Weinheim, 1988; for TFA from *Trifluoroacetic Acid* by John B. Milne In *Chemistry of Non-Aqueous Solvents,* Vol 5B; J. J. Lagowski, Ed.; Academic Press: New York, 1978; pp 1–52; and for nonanoic acid from G. Geisler and E. Manz, *Monat Chem.* 1969, 100, 1133–39. NMP is N-methylpyrrolidinone.

An important advantage of the present invention is that the high rates of esterification in TFA allow novel esterification processes to be carried out at relatively low temperature, e.g., temperatures in the range of about –10 to 80° C., preferably temperatures of about 0 to 50° C., which results in improved selectivity to the desired product of higher quality due to the avoidance or minimization of the formation of color bodies. However, if desired, the process may be carried out over a broad range of temperatures, e.g., temperatures of about –50 to 250° C. Esterification at higher temperature may be preferred in the design of a continuous process in which the size of reaction vessels must be minimized. Pressure is not an important aspect of the present invention and, thus, the process may be carried out at pressures moderately above or below ambient temperature.

A further advantage of the present invention is its applicability to a mixture of esterification agents derived from mixtures of carboxylic acids. Because fatty acids (especially from natural sources) are often obtained as mixtures of carboxylic acids, the ability to convert such mixtures, via mixtures of carboxylic acid anhydrides and halides, to their corresponding mixtures of benzenesulfonate esters offers a great advantage to a manufacturer that wishes to utilize such low cost feedstocks. As described above, TFA is readily removed by evaporation under mild conditions so purification of the products to high purity white powders is vastly simplified. The method of the present invention is readily applied to the manufacture of products containing a mixture of benzenesulfonate esters.

The process may be carried out as a batch process or in a continuous or semi-continuous mode of operation. Batch operation is illustrated in the examples presented herein. In continuous operation of the process, a mixture of a phenol and TFA are treated with the esterification agent in an esterification reactor that is appropriately agitated so that the initial slurry is well mixed. With adequate time in the esterification reactor a solution is produced which can be, for instance in the case of benzenesulfonate esters, spray-dried to remove nearly all TFA, e.g., >90%. The solid product may be further dried of TFA by, for instance, a fluidized-bed drier which can reduce the residual TFA is solid products to significantly less than 2%. Such solid products typically are very white (L>90 on the Hunter $L_{ab}$ color scale). When a carboxylic acid anhydride is used as the esterification agent in my novel process, the TFA may be removed with a solvent substitution procedure using a higher boiling poor solvent such as propionic acid to produce a filterable, purified solid product which may be isolated via continuous centrifugation and further dried by a fluidized-bed drier.

EXAMPLES

The process provided by the present invention is further illustrated by the following examples. The following abbreviations are used in the examples: TFA=trifluoroacetic acid, TFAA=trifluoroacetic acid anhydride, and SPS=sodium 4-phenolsulfonate. All NMR spectra were obtained on a Varian Gemini 300 NMR spectrometer with samples dissolved in $d_6$-DMSO, unless otherwise indicated. Chemical shifts ($\delta$) are referenced to residual protons in $d_6$ DMSO at 2.50 ppm and the carbon signal of DMSO at 39.51 ppm. Procedures are not optimized with respect to yields, which are reported relative to the conversion of SPS.

Reference Example 1

Nonanoic anhydride (9.78 g, 0.062 moles) and TFAA (18 ml, 0.127 moles) and 50 ml dichloromethane were placed in a 100 ml flask. After ten minutes at room temperature this flask was heated to rapidly remove the volatiles at 40° C. The flask was cooled with an ice-bath and low boiling materials were removed at reduced pressure. The flask then was heated and 12.0 g, corresponding to a 76% yield, of nonanoyl trifluoroacetate, boiling at 50–55° C. (0.5 torr) were collected. $^1$H NMR (CDCl$_3$): $\delta$2.61 (t, 7.4, 2H), 1.72 (p, 7.4, 2H), 1.29 (m, 10H), 0.89 (t, 7.1, 3H); $^{13}$C NMR (CDCl$_3$): $\delta$165.7, 152.9 (q, 44.7), 114.0 (q, 286.3), 35.2, 31.9, 29.22, 29.19, 28.8, 24.0, 22.8, 14.2; IR $\nu_{c=o}$ (cyclohexane)=1853, 1786 cm$^{-1}$.

Reference Example 2

The procedure described in Reference Example 1 was repeated using an equivalent amount of hexanoic anhydride to produce hexanoyl trifluoroacetate: b.p.=30–35° C. (1.0 mm) $^1$H NMR (CDCl$_3$): $\delta$2.61 (t, 7.4, 2H), 1.72 (p, 7.4, 2H), 1.30 (m, 8H), 0.89 (t, 3H)); $^{13}$C NMR (CDCl$_3$): $\delta$165.7, 152.9 (q, 44.7), 114.0 (q, 286.3), 35.2, 31.7, 28.9, 24.0, 22.8, 14.2; IR $\nu_{c=o}$ (cyclohexane)=1854, 1786 cm$^{-1}$.

Reference Example 3

The procedure described in Reference Example 1 was repeated using an equivalent amount of octanoic anhydride to produce octanoyl trifluoroacetate: b.p.=40–45° C. (1.5 mm) $^1$H NMR (CDCl$_3$): $\delta$2.61 (t, 7.4, 2H), 1.72 (p, 7.4, 2H), 1.30 (m, 8H), 0.89 (t, 3H)); $^{13}$C NMR (CDCl$_3$): $\delta$165.7, 152.9 (q, 44.7), 114.0 (q, 286.3), 35.2, 31.7, 28.9, 28.8, 24.0, 22.7, 14.2; IR $\nu_{c=o}$ (cyclohexane)=1854, 1786 cm$^{-1}$.

Reference Example 4

The procedure described in Reference Example 1 was repeated using an equivalent amount of decanoic anhydride to produce decanoyl trifluoroacetate: b.p.=70° C. (0.5 mm) $^1$H NMR (CDCl$_3$): $\delta$2.61 (t, 7.4, 2H), 1.72 (p, 7.4, 2H), 1.29 (m, 10H), 0.89 (t, 3H); $^{13}$C NMR (CDCl$_3$): $\delta$165.7, 152.8 (q, 45.2), 113.9 (q, 286.3), 35.2, 32.0, 29.47, 29.37, 29.26, 28.8, 24.0, 22.8, 14.3; IR $\nu_{c=o}$ (cyclohexane)=1854, 1786 cm$^{-1}$.

Example 1

A 300-ml, round-bottom flask with a nitrogen inlet and a magnetic stir bar was flushed with nitrogen for ten minutes. SPS (34.92 g, 0.18 moles) and TFA (158 ml, TFA:SPS mole ratio=7.7:1) were placed in the flask which was sealed with a septum cap and the resulting slurry was stirred while being cooled by an ice-water bath. A single rapid addition of nonanoyl trifluoroacetate (50.0 g, 0.18 mole) was made via syringe. After ten minutes with the reaction mixture at 5° C., a sample was withdrawn for assay by $^1$H NMR. At this point 100% of the SPS has been converted to NOBS. The mixture was warmed to ambient temperature and the volatiles were removed by rotary evaporation yielding NOBS as a white residue.

Example 2

A 300-ml, round-bottom flask with a nitrogen inlet and a magnetic stir bar was flushed with nitrogen for ten minutes. SPS (5.09 g, 25.9 millimoles—mmol) and TFA (30 ml) were placed in the flask which was sealed with a septum cap and the resulting slurry was stirred while being cooled by an ice-water bath. A single rapid addition of nonanoic anhydride (8.5 ml, 25.9 mmoles) was made via syringe. Within one minute the slurry is dissolved to yield a homogeneous solution. The stirring was continued for five minutes. The volatiles were removed by rotary evaporation yielding a white residue to which was added 100 ml of acetone. The solids were collected on a Buchner funnel and dried under reduced pressure yielding 8.06 g of sodium 4-(nonanoyloxy) benzenesulfonate (92% yield). NMR analysis shows complete conversion of the SPS to NOBS. $^1$H NMR (DMSO): $\delta$7.63, d (8.3, 2H); 7.05, d (8.2, 2H); 2.56, t (7.4, 2H); 1.63, m (2H); 1.27 (10H) and 0.86, t (3H). SPS: $^1$H NMR (DMSO): $\delta$7.38, d (8.0, 2H) and 6.65, d (8.8, 2H). $^{13}$C NMR(DMSO): $\delta$171.7, 150.4, 126.9, 121.0, 33.4, 31.2, 28.7, 28.5, 28.4, 24.3, 22.1 and 14.0 ppm.

Example 3 and Comparative Examples 1–4

To demonstrate the advantage of operating the esterification process in the presence of TFA, a series of substantially identical experiments were carried out using different carboxylic acids. SPS (0.5 g, 2.5 mmol) and 3.0 g of the carboxylic acid were placed in a 15 ml vial. Nonanoic anhydride (1.00 ml, 3.0 mmol) was added via syringe, the vial was capped and placed in an oil bath at 50° C. for five minutes and then quenched with 10 ml of a 30% aqueous acetonitrile solution. The volatile materials were stripped from this product solution and the conversion of SPS to sodium 4-(nonanoyloxy)-benzenesulfonate (NOBS) in the resulting residue was analyzed by integration of the aromatic region of the $^1$H NMR. The carboxylic acids used, the aqueous $pK_a$ of each and the relative activity of each with reference to the activation produced by TFA are set forth in Table 2.

TABLE 2

| Example | Carboxylic Acid | Aqueous $pK_a$ | Relative Activity |
|---|---|---|---|
| 3 | $CF_3CO_2H$ | 0.22 | 1.00 |
| C-1 | $CCl_3CO_2H$ | 0.64 | 0.58 |
| C-2 | $F_2HCO_2H$ | 1.31 | 0.22 |
| C-3 | $C_8H_{17}CO_2H$ | 4.86 | 0.00 |
| C-4 | $CH_3CO_2H$ | 4.75 | 1.00 |

Examples 4 and 5 and Comparative Examples 5–8

A series of substantially identical experiments were carried out using varying amounts of TFA to demonstrate that minor amounts of TFA do not provide the advantages of the present invention. SPS (0.5 g, 2.5 mmol) and 3.0 g of a mixture of TFA and nonanoic acid were placed in a 15 ml vial with a magnetic stir bar (oven-dried). Nonanoic anhydride (1.00 ml, 3.0 mmol) was added via syringe, the vial was capped and placed in an oil bath at 50° C. for five minutes and then quenched with 10 ml of a 30% aqueous acetonitrile solution. The volatile materials were stripped from this product solution and the conversion of SPS to sodium 4-(nonanoyloxy)benzenesulfonate (NOBS) in the resulting residue was analyzed by integration of the aromatic region of the $^1$H NMR. The amount of TFA used (g), the TFA:SPS mole ratio, and the percent conversion of SPS to NOBS (% Conv) for each of Examples 4 and 5 and Comparative Examples 5–8 is shown in Table 3. Comparative Example 6 (C-6) was carried out for 12 hours as a control.

TABLE 3

| Example | g TFA | TFA:SPS Ratio | % Conv |
|---|---|---|---|
| C-5 | 0.00 | — | 0 |
| C-6 | 0.03 | 0.10:1 | 0 |
| C-7 | 0.30 | 1.03:1 | 0 |
| C-8 | 0.75 | 2.58:1 | <5 |
| 4 | 1.50 | 5.15:1 | 35 |
| 5 | 3.00 | 10.31:1 | 54 |

Example 6

A 300-ml, round-bottom flask with a nitrogen inlet and a magnetic stir bar was flushed with nitrogen for ten minutes. SPS (34.92 g, 0.18 moles) and TFA (158 ml) were placed in the flask which was sealed with a septum cap and the resulting slurry was stirred while being cooled by an ice-water bath. A single rapid addition of nonanoyl chloride (31.5 g, 0.18 mol) was made via syringe. After ten minutes with the reaction mixture at 5° C. a sample was withdrawn for assay by $^1$H NMR. At this point 60% of the SPS has been converted to NOBS. The mixture was warmed to ambient temperature and the volatiles were removed by rotary evaporation yielding a white residue. The solids were collected on a Buchner funnel and dried under reduced pressure yielding 8.06 g of sodium 4-(nonanoyloxy)benzene-sulfonate (92% yield).

Example 7

A 100-ml, round-bottom flask with a nitrogen inlet and a magnetic stir bar was flushed with nitrogen for ten minutes. SPS (5.47 g, 0.027 moles), $K_2CO_3$ (3.72 g, 0.027 mol) and TFA (34.3 ml) were placed in the flask which was sealed with a septum cap and the resulting slurry was stirred while being cooled by an ice-water bath. A single rapid addition of nonanoyl chloride (4.64 g, 0.026 mol) was made via syringe. After fifteen minutes with the reaction mixture at 5° C. a sample was withdrawn for assay by $^1$H NMR. At this point 18% of the SPS has been converted to NOBS.

Comparative Example 9

A 300-ml, round-bottom flask with a nitrogen inlet and a magnetic stir bar was flushed with nitrogen for ten minutes. SPS (9.10 g, 46.4 mmol), $K_2CO_3$ (6.35 g, 45.9 mmol), and 40 ml toluene were placed in the flask which was sealed with a septum cap and the resulting slurry was stirred at ambient temperature. A single rapid addition of nonanoyl chloride (7.92 g, 44.8 mmol) was made via syringe. After twenty minutes at 23° C. a sample of the reaction mixture was withdrawn for assay by $^1$H NMR. At this point there was no conversion of the SPS to NOBS. The mixture was heated to reflux (111° C.) for 53 minutes and a second sample was assayed. $^1$H NMR showed 72 % conversion of SPS to NOBS, consistent with results reported in U.S. Pat. No. 5,069,828. This example shows that the reaction of nonanoyl chloride with SPS without TFA is significantly slower than when TFA is used as a solvent.

The invention has been described in detail with particular reference to preferred embodiments thereof, but it will be understood that variations and modifications can be effected within the spirit and scope of the invention.

What is claimed is:

1. A process for the preparation of an aryl carboxylate ester which comprises reacting a phenol with an esterification agent selected from carboxylic acid anhydrides containing a total of up to about 40 carbon atoms and carboxylic acid halides containing a total of up to about 20 carbon atoms in the presence of trifluoroacetic acid (TFA), wherein the amount of TFA present initially and during the process gives a TFA:phenol reactant mole ratio of about 2:1 to 20:1, and the process is carried out in the absence of trifluoro acetic anhydride.

2. A process according to claim 1 wherein the esterification agent is an aliphatic carboxylic acid anhydride containing a total of about 12 to 32 carbon atoms and the carboxylic acid anhydride:phenol mole ratio is about 0.5:1 to 3:1.

3. A process for the preparation of an aryl carboxylate ester which comprises reacting a phenol with a carboxylic acid anhydride in the presence of trifluoroacetic acid (TFA) wherein the amount of TFA present initially and during the process gives a TFA:phenol reactant mole ratio of about 2:1 to 20:1, the phenol reactant is phenol, a hydroxybenzene sulfonic acid or an alkali hydroxybenzenesulfonate; the carboxylic acid anhydride reactant is an alkanoic acid anhydride wherein each of the two alkanoic acid residues of the anhydride contains about 6 to 16 carbon atoms and is either unsubstituted or substituted with an alkanoylamido group containing up to about 12 carbon atoms; and the process is carried out in the absence of trifluoroacetic anhydride.

4. A process according to claim 3 wherein the process is carried out at a temperature of about 0 to 50° C. and the carboxylic acid anhydride:phenol mole ratio is about 0.5:1 to 3:1.

5. A process according to claim 4 wherein the phenol reactant is phenol, a hydroxybenzenesulfonic acid, a sodium hydroxybenzene-sulfonate or a potassium hydroxybenzenesulfonate; and the carboxylic acid anhydride reactant is an alkanoic acid anhydride wherein each of the two alkanoic acid residues of the anhydride contains about 6 to 16 carbon atoms and is unsubstituted.

6. A process according to claim 3 wherein the phenol reactant is phenol, a hydroxybenzene sulfonic acid or a sodium hydroxybenzenesulfonate or a potassium hydroxybenzenesulfonate; and the carboxylic acid anhydride reactant is an akanoic acid anhydride wherein each of the two alkanoic acid residues of the anhydride contains about 6 to 16 carbon atoms and is substituted with an alkanoylamido group containing up to about 12 carbon atoms.

7. A process for the preparation of an aryl carboxylate ester which comprises reacting a phenol with a carboxylic acid chloride in the presence of trifluoroacetic acid (TFA) wherein the amount of TFA present initially and during the process gives a TFA:phenol reactant mole ratio of about 2:1 to 20:1; the phenol reactant is phenol, a hydroxybenzene sulfonic acid or an alkali hydroxybenzenesulfonate; the carboxylic acid halide reactant is an alkanoic acid chloride wherein the alkanoic acid residue of the acid chloride contains about 6 to 16 carbon atoms and is either unsubstituted or substituted with an alkanoylamido group containing up to about 12 carbon atoms; and the process is carried out in the absence of trifluoroacetic anhydride.

8. A process according to claim 7 wherein the process is carried out at a temperature of about 0 to 50° C. and the carboxylic acid chloride:phenol mole ratio is about 0.5:1 to 3:1.

9. A process according to claim 8 wherein the phenol reactant is phenol, a hydroxybenzenesulfonic acid, a sodium hydroxybenzene-sulfonate or a potassium hydroxybenzenesulfonate; and the carboxylic acid halide reactant is an alkanoic acid chloride wherein the alkanoic acid residue of the acid chloride contains about 6 to 16 carbon atoms and is unsubstituted.

10. A process according to claim 8 wherein the phenol reactant is phenol, a hydroxybenzene sulfonic acid, a sodium hydroxybenzene-sulfonate or a potassium hydroxybenzenesulfonate; and the carboxylic acid halide reactant is an alkanoic acid chloride wherein the alkanoic acid residue of the acid chloride contains about 6 to 16 carbon atoms and is substituted with an alkanoylamido group containing up to about 12 carbon atoms.

11. A process for the preparation of an aryl carboxylate ester which comprises reacting a phenol with a mixed anhydride having the formula:

$$R-C(O)-O-C(O)-CF_3 \tag{I}$$

in the presence of TFA, wherein R is an aliphatic, cycloaliphatic or aromatic group containing up to about 19 carbon atoms; the amount of TFA present initially and during the process gives a TFA:phenol reactant mole ratio of about 2:1 to 20:1; and the process is carried out in the absence of trifluoroacetic anhydride.

12. A process according to claim 11 wherein the R is an aliphatic group containing 5 to 15 carbon atoms and the mixed anhydride:phenol mole ratio is about 0.5:1 to 3:1.

13. A process for the preparation of an aryl carboxylate ester which comprises reacting a phenol with a mixed anhydride having the formula:

$$R-C(O)-O-C(O)-CF_3 \tag{I}$$

in the presence of trifluoroacetic acid (TFA) wherein the amount of TFA present initially and during the process gives a TFA:phenol reactant mole ratio of about 2:1 to 20:1; the phenol reactant is phenol, a hydroxybenzene sulfonic acid or an alkali hydroxybenzenesulfonate; R is an alkyl group which contains about 5 to 15 carbon atoms and is either unsubstituted or substituted with an alkanoylamido group containing up to about 12 carbon atoms; and the process is carried out in the absence of trifluoroacetic anhydride.

14. A process according to claim 13 wherein the process is carried out at a temperature of about 0 to 50° C. and the mixed anhydride:phenol mole ratio is about 0.5:1 to 3:1.

15. A process according to claim 14 wherein the phenol reactant is phenol, a hydroxybenzenesulfonic acid, a sodium hydroxybenzenesulfonate or a potassium hydroxybenzenesulfonate; and R is an alkyl group which contains about 5 to 15 carbon atoms and is unsubstituted.

16. A process according to claim 14 wherein the phenol reactant is phenol, a hydroxybenzene sulfonic acid, a sodium hydroxybenzenesulfonate or a potassium hydroxybenzenesulfonate; and R is an alkyl group which contains about 5 to 15 carbon atoms and is substituted with an alkanoylamido group containing up to about 12 carbon atoms.

* * * * *